United States Patent [19]

Shea

[11] 4,166,084
[45] Aug. 28, 1979

[54] BUBBLE MAKER

[76] Inventor: Melvin E. Shea, 85 Terrace Rd., Milford, Conn. 06460

[21] Appl. No.: 889,642

[22] Filed: Mar. 24, 1978

[51] Int. Cl.² .................... B67D 5/34; A63H 33/28
[52] U.S. Cl. ..................... 261/69 A; 46/6;
137/87; 222/57; 222/133; 239/412; 261/112
[58] Field of Search .................. 261/69 R, 69 A, 110,
261/112, 78 A; 46/6–8; 137/87, 114, 604;
222/57, 129.2, 133; 239/412, 432, 434, 570

[56] References Cited

U.S. PATENT DOCUMENTS

| 143,432 | 10/1873 | Bliss | 46/7 |
|---|---|---|---|
| 642,892 | 2/1900 | Bliss | 46/7 |
| 1,115,556 | 11/1914 | Little | 46/6 |
| 1,330,701 | 2/1920 | Gilchrist | 46/7 |
| 1,339,798 | 5/1920 | Thompson | 137/87 |
| 1,478,792 | 12/1923 | Ogden | 137/87 |
| 1,524,217 | 1/1925 | Small | 137/87 |
| 2,205,028 | 6/1940 | Bloxom | 46/6 |
| 2,305,382 | 12/1942 | Hagopian | 46/6 |
| 2,587,536 | 2/1952 | Scott | 46/8 |
| 2,615,464 | 10/1952 | Hughey | 137/87 |
| 3,025,669 | 3/1962 | Fischoff | 137/114 |
| 3,422,834 | 1/1969 | Garabello | 137/114 |
| 3,443,337 | 5/1969 | Ehrlich | 46/6 |

FOREIGN PATENT DOCUMENTS 24679 of 1897 United Kingdom .................. 46/8

Primary Examiner—Frank W. Lutter
Assistant Examiner—Gregory N. Clements

[57] ABSTRACT

A Bubble Maker to be used for adding air fresheners, deodorants, cleaners, perfume or water to air space in the form of bubbles which are then absorbed into the space to be treated.

1 Claim, 2 Drawing Figures

BUBBLE MAKER

For reasons of health and comfort it is desirable to treat the air we breathe in living and working space areas, including hospitals, sick rooms and operating and surgical areas; by adding to it fresheners, deodorants, cleaners, perfume or water for humidity. In hospital use it could be water from which all impurities have been removed. This invention is a device which accomplishes this effectively and easily by placing the above ingredients into the air in the form of tiny bubbles which are then very readily absorbed into the space to be conditioned.

In the accompanying drawing.

Figure 1:
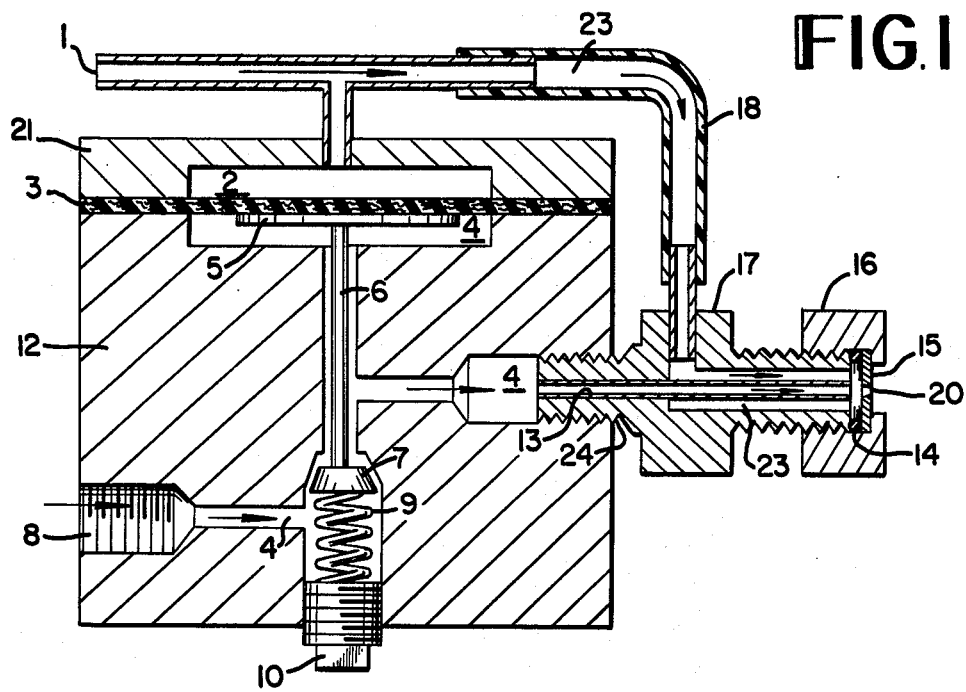
FIG. 1 is a half section diagrammatic view of the device and shows all the parts of the invention except Threaded Members 22.
Figure 2:
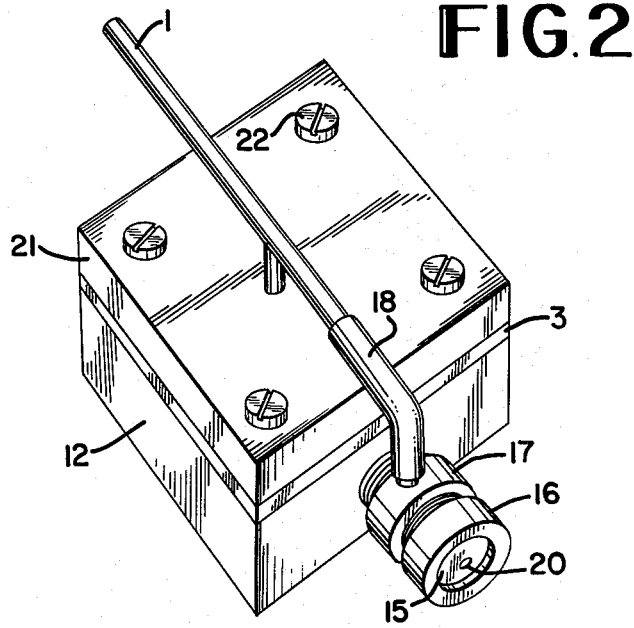
FIG. 2 is a perspective view of the same device and this view shows Threaded Members 22.

Different pieces of the device are held together as follows: Orifice plate 15 is held in place by threaded cap 16 and sealed against leakage by O-ring 14 which is compressed between orifice body 17 and orifice plate 15. Orofice body 17 is attached to the main body 12 of the device by threaded pipe joint 24. The cap 21 is attached to the main body by threaded members 22. The cap 21 is connected to orifice body 17 by slip tubing 18. Capillary tube 13 is pressed fit into orifice body 17.

The liquid supply line to this device is fed from the water main at water main pressure and a chemical reservoir from which the chemical is metered and injected into the liquid supply line in quantity and type needed for the particular requirements necessary to condition the air in the space to be treated.

The device is activated when a motor driven compressor is turned on supplying air to the air inlet 1. This can be done manually or automatically. The air flows from air inlet at 1 through tubing 18 to orifice 20 and through same meanwhile pressurizing the air passageway 23 in the unit. This in turn pressurizes air chamber 2, depressing flexible diaphragm 3 and bearing plate 5 and push rod 6 opening valve stopper 7 and allowing liquid to flow into liquid passways 4 and to pressurize same.

The liquid pressure below diaphragm 3 is governed by the air pressure above the diaphragm 3 in air chamber 2. As the liquid pressure increases, it raises diaphragm 3, bearing plate 5, push rod 6, and stopper 7, reducing the flow of liquid until the liquid pressure 4 below diaphragm 3 is balanced with the air pressure in air passways 23 and in chamber 2.

The liquid flows through liquid passways 4, and through capillary tube 13, depositing the liquid in a film on orifice plate 15. The air from inlet 1 flows through air passageway 23, and into orifice body 17, forcing its way through the film of liquid on orifice plate 15 and through orifice 20, and in doing so it forms and emits the bubbles that carry the liquid into the air space that is to be treated.

When the device is de-activated, the compressor is simply, manually or automatically, turned off. The pressurized air remaining in chamber 2 and passageway 23 is discharged through orifice 20, with no pressure now above diaphragm 3 the coil spring 9, which is made with enough tension to lift the weight of the stopper 7 and rod 6, reseats stopper 7 which is then held firmly closed by liquid at water main pressure from inlet 8 and the coil spring 9.

Any pressurized air remaining in the device is discharged through orifice 20.

What is claimed is:

1. A bubble making device to combine liquid and compressed air into tiny bubbles and to blow said bubbles into the air in the space to be conditioned, said liquid being fed to the device from a water main from a municipal reservoir or other suitable major water supply source, through a liquid supply line, said liquid supply line being pipe or tubing of metal or plastic, into which a prescribed additive is being metered and injected as used by a suitable chemical solution feeder in the amount required to condition or treat the air in a specified space, said compressed air being fed to the device from a suitable properly sized motor driven air compressor through an air line, said air line being of metal or plastic tubing, in the amount required, said device comprising the following parts; a main body formed from a block of metal or plastic and containing a vertical tubular passway, said vertical tubular passway being formed with three diameters of differing dimensions, the lower section of said vertical tubular passway being of a larger diameter than the middle section provides a seat where these two differing diameters meet, the upper section of the vertical tubular passway extends through the top of the main body and is increased in diameter and to a depth to form a reservoir of a size suitable to allow for free movement of a flexible diaphragm, said diaphragm being formed from a clothlike rubberized waterproof material, and a bearing plate, said bearing plate being a flat metal disc affixed by riveting or other suitable means to the middle of said flexible diaphragm, said vertical tubular passway is connected to two horizontal tubular passways at different levels within the main body, the lower horizontal tubular passway is connected to the liquid supply line by threaded joint and joins the vertical tubular passway at a point below the seat, the upper horizontal tubular passway is connected to the orifice body by threaded joint and joins the vertical tubular passway at a point immediately above the seat, the lower section of the vertical tubular passway extends through the bottom of the main body and is fitted with a plug by a threaded joint, said plug being of metal or plastic, said plug supports a coil spring, a rubber stopper and a push rod, said rubber stopper is fastened to the bottom end of the push rod by threaded joint, said push rod being a brass rod of a length to extend to a point immediately below and adjacent to the bearing plate and flexible diaphragm, said flexible diaphragm being compressed between the abutting parts of the main body and the cap, said cap being formed from same type structural element as the main body, said main body cap and flexible diaphragm being further fastened together by threaded members, said cap being formed with an opening in its lower face of the same dimensions as the opening in the upper section of the vertical tubular passway in the main body, said openings in the main body and the cap are formed to align with each other to form a chamber, said chamber is separated top from bottom by the flexible diaphragm, the upper half of said chamber forming an air chamber, the lower half of said chamber forming a liquid reservoir, a vertical tubular passageway is provided from the top of the air chamber through the top of the cap, the opening from this vertical passageway is fitted with a "tee" fitting, said "tee" fitting being of plastic or metal and being formed to accomodate tubing, an opening from said "tee" fitting is connected by metal or plastic tubing to the air compressor, the remaining opening from said "tee" fitting is connected by metal or plastic tubing to the orifice body, said orifice body being of plastic or metal and conforming to the main body, said orifice body is connected to the main body at the outer end of the upper horizontal tubular passway by threaded joint, the opposite end of said orifice body contains the orifice plate, said orifice plate being a flat circular disc made of metal or plastic, an orifice, said orifice being a tiny drilled hole directly through the middle of the orifice plate, a threaded cap, said threaded cap made of metal or plastic to conform to the orifice body, said threaded cap being formed with an opening in its normally closed head, said opening is of a smaller diameter than the orifice plate and is formed into a seat to hold said orifice plate in its place at the outer end of the orifice body while leaving the orifice unobstructed on its outer side, said threaded cap is fastened to the orifice body by threaded joint, an "O" ring being a gasket of plastic or rubber is compressed between the orifice body and the orifice plate by threaded cap and orifice plate, said "O" ring seals the orifice body and orifice plate from leakage, an air passageway being a horizontal tubular passageway within the orifice body and extending from the orifice plate to a point midway in the length of the orifice body where it joins the vertical section of the tubular passageway which is connected to the "tee" fitting as previously recited, a capillary tube is press fitted through the orifice body from the end which attaches to the main body and extends centrally and through the air passageway in the orifice body to a point adjacent to the orifice, said capillary tube being of plastic or metal is sized to deliver a minute quantity of liquid, said minute quantity being approximately one part of liquid to seventy parts of air, delivered to the orifice by volume, said air being delivered when the compressor is energized, either by manual or by automatic means, feeding compressed air to the air inlet at the "tee" fitting in the cap, then through said "tee" and through the tubing and into the orifice body, to the orifice plate and through the orifice, the small diameter of the orifice restricts the flow of air through said orifice causing pressurization of the air passageway and the air chamber above the flexible diaphragm, the increased air pressure above the diaphragm depresses said diaphragm, which depresses the bearing plate, the push rod and the stopper, thereby opening the seat in the vertical tubular passway and allowing the liquid to flow from the liquid supply line through the lower horizontal passway and into the vertical tubular passway past the seat and stopper then into the liquid reservoir below the diaphragm and through the upper horizontal passway, then through the capillary tube, the capillary tube restricts the flow of liquid causing increased pressure in the liquid reservoir below the diaphragm, said increased pressure raising the diaphragm and bearing plate allowing the coil spring to raise the push rod and stopper thereby restricting the flow of liquid into the reservoir and through the capillary tube until the pressure below the diaphragm is in a balance with the pressure above the diaphragm, the minute amount of liquid passing through the capillary tube and being deposited on the orifice plate and over the orifice maintains a film of liquid on said orifice plate and overspreading the orifice, the greater volume of air being delivered through the orifice takes with it the minute amount of liquid as it is being deposited on the orifice plate and over-spreading the orifice and assures that the deposit cannot increase to more than a film, the tendency of this film to cling to the orifice plate and to the perimeter of the orifice while the air is discharging through the center of the orifice causing the formation of the tiny bubbles, which are being blown en masse into the air in the space to be conditioned, continuously, until the device is shut down, said shut down is accomplished by interrupting the energy supply to the compressor thereby interrupting the flow of compressed air into the device and as the pressurized air remaining in the air passageway discharges through the orifice, the air pressure in the chamber above the flexible diaphragm lowers relieving the pressure on said flexible diaphragm and bearing plate allowing the coil spring to raise the push rod and to seat the stopper, the combination of the liquid pressure below the stopper and the tension of the coil spring keeps the liquid supply firmly shut off, meanwhile if any volume of pressurized air remains in the air passageway and air chamber of the device it continues discharging through the orifice taking with it any minute amount of liquid remaining in the orifice thereby eliminating problems that may arise from said liquid drying and solidifying in said orifice.

* * * * *